US00PP32070P2

(12) United States Plant Patent
Hansen

(10) Patent No.: US PP32,070 P2
(45) Date of Patent: Aug. 11, 2020

(54) **X *MANGAVE* PLANT NAMED 'SPONGE PAINT'**

(50) Latin Name: **x *Mangave* times *Agave* hybrid**
Varietal Denomination: Sponge Paint

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/602,655

(22) Filed: Nov. 15, 2019

(51) Int. Cl.
*A01H 6/12* (2018.01)
*A01H 5/00* (2018.01)

(52) U.S. Cl.
USPC ..... Plt./373

(58) Field of Classification Search
CPC ..... A01H 6/12; A01H 5/00
See application file for complete search history.

*Primary Examiner* — Annette H Para

(57) ABSTRACT

A new and unique x *Mangave* plant named 'Sponge Paint' characterized by a rounded mound of oblanceolate to rhombic, fleshy, slightly-rough leaves that develop silver-gray coloration with small wine-colored spots in strong ultraviolet light. Leaves have medium-sized, sharp, firm marginal teeth and firm, sharp, apical spine. The new plant is suitable for the garden or as a potted plant in the garden or home.

1 Drawing Sheet

Botanical classification: x *Mangave* times *Agave* hybrid.
Variety denomination: 'Sponge Paint'.

STATEMENT REGARDING PRIOR DISCLOSURES UNDER 37 CFR 1.77(B)(6)

The first disclosure of the claimed plant, in the form of a private sale, was made by Walters Gardens, Inc. on Feb. 4, 2019 to Plant Delights Nursery, Inc. The first public disclosure of x *Mangave* 'Sponge Paint' was early on Feb. 14, 2019 as a brief description and photo on a website operated by Walters Gardens, Inc. Information for this website and plants for this sale were obtained from the inventor. No plants of x *Mangave* 'Sponge Paint' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Sponge Paint' that was hybridized by the inventor at a wholesale perennial nursery in Zeeland, Mich., USA as a cross between a proprietary, unreleased hybrid selection of x *Mangave* assigned the breeder code 12-6-4 (not patented) as the female or seed parent times and *Agave potatorum* 'Bluewinds' (not patented) as the male or pollen parent. The cross was performed Nov. 17, 2014 and seeds were harvested and sown later the following spring. Through trials at the same nursery the plant was assigned the breeder code 15-47-23. The new plant has been successfully asexually propagated by removal of basal offsets and sterile shoot-tip tissue culture at the same nursery in Zeeland, Mich. The asexual tissue culture propagation has been found to produce stable and identical plants that maintain all the unique characteristics of the original plant.

BRIEF SUMMARY OF THE INVENTION

'Sponge Paint' differs from its parents as well as all other *Manfreda, Agave* and x *Mangave* known to the applicant. The female parent has a more upright habit with longer, arching, narrower and thinner leaves with more burgundy spots. The male parent is shorter and more compact in habit with foliage that is shorter, more obovate, has a creamy white margin and lacks the greyed-purple spotting on the upper and lower surfaces. The nearest comparison plants are: 'Tooth Fairy' U.S. Plant Pat. No. 29,599, 'Purple People Eater' U.S. Plant Pat. No. 29,949 and 'Moonglow' U.S. Plant Pat. No. 29,195. 'Tooth Fairy' has a taller habit, narrower foliage with larger teeth and apical spines and without greyed-purple spotting. 'Purple People Eater' has larger less compact habit, the foliage is slightly folded longitudinally, the marginal teeth are semi-flexible and more greyed-orange, and the leaves have a glaucous greenish-purple as well as spotted with greyed-purple. 'Moonglow' has flatter habit, narrower foliage with larger greyed-purple spotting.

'Sponge Paint' is unique from all of the above cultivars and all *Agave*, x *Mangave* and *Manfreda* known to the inventor by the following combined traits:

1. Rounded mound of oblanceolate to rhombic, sarcous, scabridulose leaves;
2. Leaves develop a silver-gray coloration with small wine-colored spots with strong ultraviolet light;
3. Leaf margins have medium-sized, sharp, firm, outward to slightly-recurved, marginal teeth and a long, firm, sharp apical spine;
4. Moderate growth rate;
5. Foliage is outwardly with distal portion slightly upwardly.

BRIEF DESCRIPTION OF THE DRAWING

The photograph of x *Mangave* 'Sponge Paint' demonstrates the overall appearance of the new plant including the unique traits as a four-year-old plant grown in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
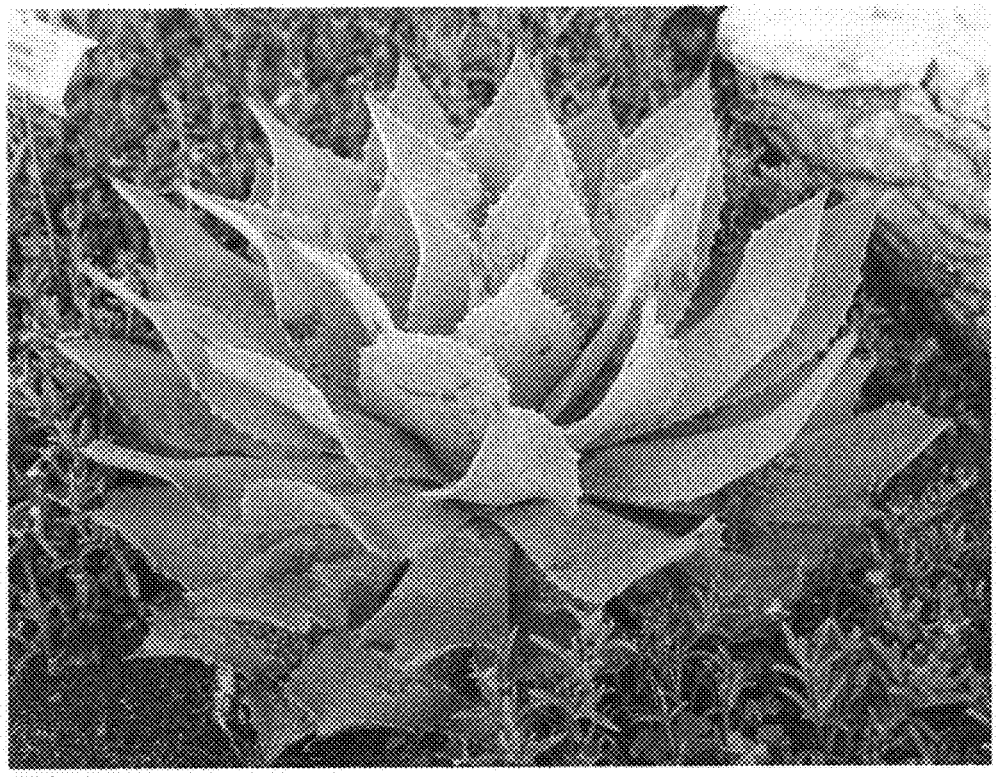
FIG. 1 shows a side view of a greenhouse grown plant that was grown in full-sun for the most recent season.
Figure 2:
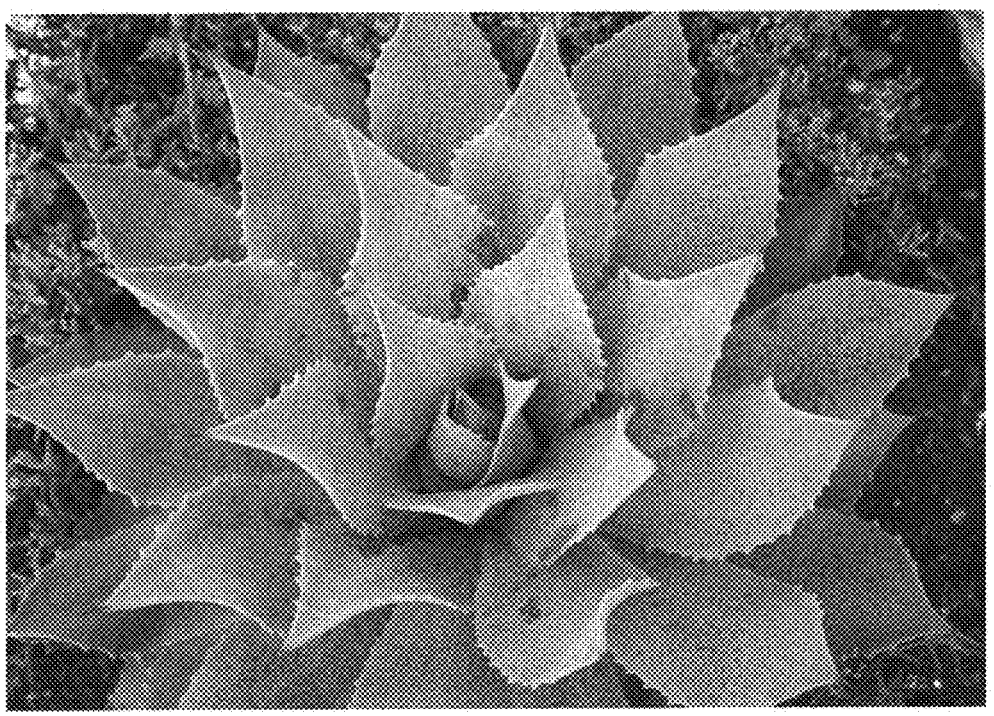
FIG. 2 shows top view of a greenhouse grown that was grown in full-sun for the most recent season.

The following descriptions and color references are based on the 2015 edition of The Royal Horticultural Society Colour Chart except where common dictionary terms are used. The new plant, x *Mangave* 'Sponge Paint', has not been observed under all possible environments. The phenotype may vary slightly with different environmental conditions, such as temperature, light, fertility, moisture and maturity levels, but without any change in the genotype. The following observations and size descriptions are of a six-year-old plant in a commercial wholesale greenhouse in Zeeland, Mich. with supplemental water and fertilizer as needed.

Parentage: A proprietary, unreleased hybrid 12-6-4 as female or seed patent and *Agave potatorum* 'Bluewinds' as the male or pollen parent;

Propagation: By sterile shoot-tip tissue culture and removal of basal offsets;

Time to initiate roots from tissue culture: About 21 days;

Growth rate: Moderate;

Crop time: About 16 to 20 weeks to finish in a 3.8 liter container from a 35 mm tissue culture growing at about 21° C.;

Rooting habit: Fleshy, lightly branching, with roots up to 30 cm long;

Root color: Nearest RHS NN155B depending on soil type;

Plant shape and habit: Succulent herbaceous perennial with basal rosettes of leaves radially emerging from central short stem in a slightly upwardly portion, producing a radially-symmetrical, compact, rounded mound;

Plant size: Foliage height about 26.0 cm tall from soil line to the top of the leaves and about 50.0 cm wide at the widest point about 15 cm above soil level;

Stem: To about 2.5 cm across; covered with leaves;

Foliage description: Oblanceolate to rhombic; simple; sessile; bi-laterally symmetrical; sarcous; scabridulose; with internal longitudinal fibers; apex acute with firm terminal spine; base truncate; with slight coarse wave; margins with medium-sized, firm, outward to slightly-recurved, marginal teeth; glabrous abaxial and adaxial; matte and scabridulose abaxial and adaxial;

Apical spine size: To about 10.0 mm long and 2.0 mm wide at base;

Marginal teeth size: Firm and sharp; about 5.0 mm long and 5.0 mm wide at base, average spacing about 6.0 mm apart;

Leaf size: To about 19.0 cm long, about 8.5 cm wide toward apical side of middle; center base about 12.0 mm thick at basal midrib; average about 17.5 cm long, 7.2 cm wide and 12.0 mm thick in longitudinal center near base; maculate adaxial and abaxial with spots of variable sizes from 0.5 mm to 3.5 mm across;

Foliage fragrance: None observed;

Leaf number: About 68 per plant;

Leaf blade color:

*Adaxial* (*low light*).—Nearest RHS 148B with spots between RHS 187A and RHS N187B.

*Abaxial* (*low light*).—Nearest blend between RHS 147B and RHS 147C with small spots nearest blend between RHS N187B and RHS N186C.

*Adaxial* (*high light*).—Nearest a blend between RHS N187C and RHS 191D with small spots nearest RHS 187A; distally developing a light blush of nearest RHS 187A with age.

*Abaxial* (*high light*).—Nearest RHS 190B with small nearest RHS 187A.

*Teeth*.—Variable with maturity; on young developing leaves and proximally on older leaves nearest RHS N155B, distally on mature leaves nearest RHS 200A.

*Terminal spine*.—On young developing leaves apex nearest RHS 173A with base nearest RHS 200A, on mature leaves nearest RHS 200A.

Petiole: Leaves sessile;

Veins: Parallel; not distinct abaxial or adaxial;

Flower description: Not yet observed;

Fruit and seed not observed;

Disease resistance: X *Mangave* 'Sponge Paint' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Sponge Paint' as herein described and illustrated.

* * * * *